(12) United States Patent
Breffa et al.

(10) Patent No.: US 8,420,588 B2
(45) Date of Patent: Apr. 16, 2013

(54) ISOSORBIDE GLYCERYL ETHER DERIVATIVES AND THEIR USE IN HOUSEHOLD APPLICATIONS

(75) Inventors: Catherine Breffa, Düsseldorf (DE); Wolfgang Poly, Düsseldorf (DE); Ansgar Behler, Bottrop (DE); Thorsten Löhl, Schmallenberg (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/394,746

(22) PCT Filed: Sep. 1, 2010

(86) PCT No.: PCT/EP2010/005368
§ 371 (c)(1),
(2), (4) Date: Mar. 7, 2012

(87) PCT Pub. No.: WO2011/029548
PCT Pub. Date: Mar. 17, 2011

(65) Prior Publication Data
US 2012/0172282 A1   Jul. 5, 2012

(30) Foreign Application Priority Data

Sep. 10, 2009   (EP) .................................... 09011586

(51) Int. Cl.
  *C11D 3/20*   (2006.01)
  *C11D 3/22*   (2006.01)
  *C11D 7/26*   (2006.01)
  *C11D 13/10*  (2006.01)
  *B08B 3/04*   (2006.01)

(52) U.S. Cl.
  USPC .......................... 510/505; 510/474; 549/464

(58) Field of Classification Search .................. 510/474, 510/505; 549/464
See application file for complete search history.

(56) References Cited

U.S. PATENT DOCUMENTS

| 3,041,300 A | 6/1962 | Morrison et al. |
| 4,891,373 A * | 1/1990 | Stoss et al. ................. 514/228.2 |
| 2002/0174596 A1 | 11/2002 | Deflort et al. |

FOREIGN PATENT DOCUMENTS

WO   WO-01/19949   3/2001

OTHER PUBLICATIONS

"International Search Report of PCT/EP2010/005368", mailed on Oct. 7, 2010, 3 pages.
Molinier, Valerie et al., "Isosorbide: A Sustainable Diol" Derived from Sorbitol for the Synthesis of New Amphiphiles, Jan. 20, 2009, 1 page.

* cited by examiner

*Primary Examiner* — Brian P Mruk
(74) *Attorney, Agent, or Firm* — Servilla Whitney LLC

(57) ABSTRACT

Disclosed are isosorbide glyceryl ether derivatives according to the following general formula (I), wherein R or R' represent a hydrogen atom, or an alkyl or an acyl group with 6 to 22 C-atoms, and n and m represent independent from each other zero, or a number from 1 to 4, and the use thereof in cleansers or detergents or personal care applications.

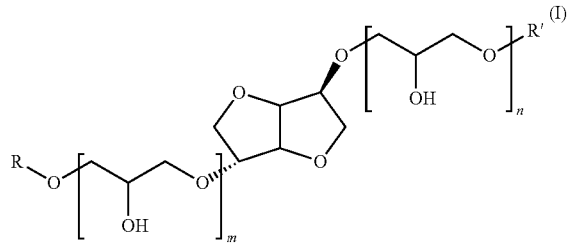

12 Claims, No Drawings

ISOSORBIDE GLYCERYL ETHER DERIVATIVES AND THEIR USE IN HOUSEHOLD APPLICATIONS

CROSS-REFERENCE TO RELATED APPLICATIONS

This application is the national stage entry of PCT/EP2010/005368, filed on Sep. 1, 2010, which claims priority to European Patent Application No. EP 09011586.6, filed on Sep. 10, 2009, both of which are incorporated herein by reference in their entireties.

FIELD

Background

The present application pertains to the use of isosorbide glyceryl ether derivatives in household products, like detergents or for cosmetic applications.

Isosorbide (or 1,4: 3,6-dianhydrosorbitol, see formula below) is the anhydride of sorbitol:

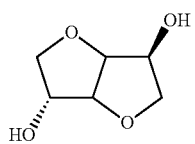

Upon heating sorbitol for example with concentrated sulfuric or hydrochloric acid, two molecules of water are eliminated with the formation of isosorbide. So far, these compounds are also known generally as dianhydrohexitols (including besides isosorbide also the isomers isomannide and isoidide). Besides isosorbide per se, certain derivatives of isosorbide are well known, inter alia mono- and diesters thereof.

Certain derivatives of isosorbide are known, especially esters or ethers thereof. Furthermore it is known to use isosorbide derivatives as additives in various applications, like detergents, cleansers or cosmetic compositions. US 2002/0174596 A1 discloses various isosorbide ethers as detergent for fuels. WO 01/0191949 A1 describes dimethylisosorbide as compound of a personal cleansing composition.

SUMMARY

One aspect of the invention relates to an isosorbide glyceryl ether derivative according to general formula (I)

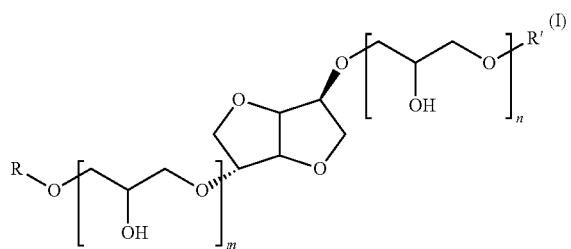

wherein R or R' represent a hydrogen atom, or an alkyl or an acyl group with 6 to 22 C-atoms, and n and m each independently represent zero, or a number from 1 to 4, with the proviso that the sum of n and m is greater than zero. A second aspect pertains to a method of preparing a cleanser, detergent or personal care composition, the method comprising using an isosorbide glyceryl ether derivative' according to an isosorbide glyceryl ether derivative described herein to prepare cleansers, detergents or personal care compositions. Yet another aspect of the invention relates to a cleanser, detergent or personal care composition comprising water, a surfactant, and at least 0.1% by weight of at least one isosorbide glyceryl ether derivative described herein.

DETAILED DESCRIPTION

Provided herein are new additives, useful in detergents and cleansers, and based on isosorbide chemistry.

The present application pertains in a first embodiment to an isosorbide glyceride according to general formula (I)

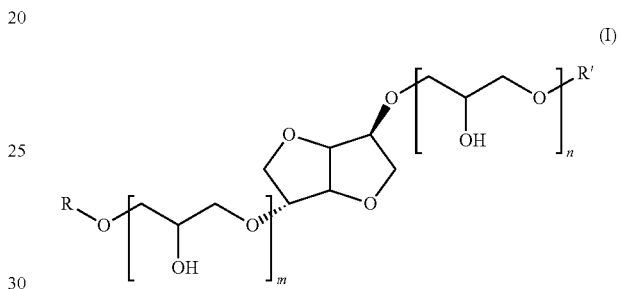

wherein R or R' represent a hydrogen atom, or an alkyl or an acyl group with 6 to 22 C-atoms, and n and m represent independent from each other zero, or a number from 1 to 4 with the proviso that the sum from n and m must be greater than zero. The compounds according to this general formula (I) are ethers of glycerol and isosorbide. They encompass both, mono- and diethers from isosorbide with glycerol, oligo-glycerol, and derivatives of glycerol, di- and oligo glycerol. The compounds may also be present as blends of different compounds of formula (I).

Preferred derivatives are those, where R and/or R' represents a linear, saturated alkyl moiety with 10 to 22, preferably 12 to 20, and most preferably 14 to 18 C-atoms. Furthermore, glycerides, i.e. the alkyl esters of glycerol or di- or oligo glycerol are preferred too. According to the way of preparation the compounds will contain besides the compounds of formula (I) lower amounts (i.e. <5 wt %) of by products and unreacted matter.

The preparation of the compounds according to formula (I) can be carried out by known processes starting from isosorbide glycidyl ethers, according to general formula (II)

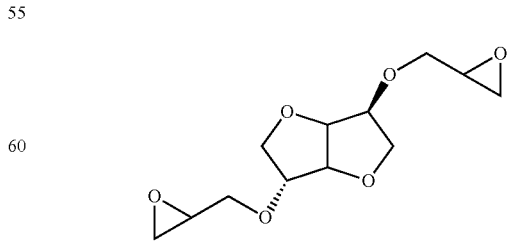

For example, according to the teaching of U.S. Pat. No. 3,041,300 an isosorbide may be reacted with epichlorohydrin in the presence of basic catalysts to obtain bisglycidyl ether according to formula (II). In a second step this oxirane ether can be cleaved by adding strong acids, like $H_2SO_4$ and the solution is then neutralized. A second way to obtain such a product is the use of alkanols in the presence of a basic catalyst.

A further embodiment of the invention pertains to the use of compounds according to formula (I) for the preparation of detergents, cleansers and the like (solid, liquid or gel-like ones) or the use of this compounds in cosmetic compositions. Furthermore, those preparations are subject matter of the present application as far as they contain water, and a surfactant and optional further common ingredients and at least one isosorbide derivate according to formula (I).

The isosorbide glyceryl ether derivatives according to formula (I) may be present in amounts from 0.1 up to 25% by weight, dependent on the particular formulation. Preferably those detergents or cleanser will contain the monoesters in amounts of 1 to 15 wt %, and most preferred from 5 to 10 wt %, based on the total weight of the cleanser or is detergent.

The isosorbide derivatives according to formula (I) are particular useful in home care applications, like detergents, and all kind of cleaners (kitchen, bathroom, hard surface, automotive or car cleansers, and multipurpose cleansers), as well as in dishwashing compositions (hand and automatic dish washing) and in personal care compositions, especially in skin and hair cleansing formulations.

Detergents according to the invention may contain, besides the isosorbide glycerides surfactants, builders, salts, bleaching agents, bleach activators, optical brighteners, redeposition inhibitors, soil repellants, solubilizers, foam inhibitors and enzymes as auxiliaries and additives.

The cleaners according to the invention may contain, for example, solubilizers, such as ethanol, isopropyl alcohol, ethylene glycol, diethylene glycol or preferably butyl diglycol, foam regulators, for example soap, soluble builders, for example citric acid or sodium citrate, EDTA or NTA, and abrasives as auxiliaries. In many cases, an additional bactericidal effect is required so that the multipurpose cleaners may contain cationic surfactants or biocides, for example glucoprotamine. The cleaners according to the invention may be both alkaline (pH>7.5) and acidic (pH<6.5). The isosorbide glyceryl ether derivatives may be formulated with other surfactants, like anionic, nonionic, amphoteric and/or cationic surfactants.

Anionic surfactants according to the present invention include aliphatic sulfates, such as fatty alcohol sulfates, fatty alcohol ether sulfates, fatty acid polyglycol ester sulfates, dialkyl ether sulfates, monoglyceride sulfates and aliphatic sulfonates, such as alkane sulfonates, olefin sulfonates, ether sulfonates, n-alkyl ether sulfonates, ester sulfonates, and lignin sulfonates. Fatty acid cyanamides, sulfosuccinic acid esters, fatty acid isethionates, acylaminoalkane sulfonates (fatty acid taurides), fatty acid sarcosinates, ether carboxylic acids and alkyl (ether) phosphates may also be used for the purposes of the invention, but are not preferred. Preferred anionic surfactants in the sense of the present invention are selected from the group of fatty alcohol sulfates, fatty alcohol ether sulfates and/or fatty acid polyglycol ester sulfates, and mixtures thereof.

Typical examples of nonionic surfactants are alkoxylates of alkanols, end-capped alkoxylates of alkanols with no free OH groups, alkoxylated fatty acid lower alkyl esters, amine oxides, alkylphenol polyglycol ethers, fatty acid polyglycol esters, fatty acid amide polyglycol ethers, fatty amine polyglycol ethers, alkoxylated triglycerides, mixed ethers and mixed formals, fatty acid-N-alkyl glucamides, protein hydrolyzates (more particularly wheat-based vegetable products), polyol fatty acid esters, sugar esters, sorbitan esters and polysorbates. If the nonionic surfactants contain polyglycol ether chains, they may have a conventional homolog distribution although they preferably have a narrow homolog distribution. The other nonionic surfactants are preferably selected from the group consisting of alkoxylates of alkanols, more particularly fatty alcohol polyethylene glycol/polypropylene glycol ethers or fatty alcohol polypropylene glycol/polyethylene glycol ethers, end-capped alkoxylates of alkanols, more particularly end-capped fatty alcohol polyethylene glycol/polypropylene glycol ethers or end-capped fatty alcohol polypropylene glycol/polyethylene glycol ethers, and fatty acid lower alkyl esters and amine oxides. Alkyl and alkenyl oligoglycosides are known, and preferred, nonionic surfactants which correspond to formula R—O—[G]$_p$ in which R is an alkyl and/or alkenyl group containing 6 to 22 carbon atoms, G is a sugar unit containing 5 or 6 carbon atoms and p is a number of 1 to 10. They may be obtained by the relevant methods of preparative organic chemistry. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (V) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl group R may be derived from primary alcohols containing 4 to 11 and preferably 8 to 10 carbon atoms.

Typical examples of cationic surfactants are quaternary ammonium compounds and quaternized fatty acid trialkanolamine esters.

Typical examples of amphoteric or zwitterionic surfactants are alkyl betaines, alkyl amidobetaines, aminopropionates, aminoglycinates, imidazolinium betaines and sulfobetaines.

The isosorbide glyceryl ether derivatives according to the present application show advantageous properties in detergents, due to their foaming properties. They could also show interesting moisturizing properties which makes it possible to use it in cosmetic preparations too.

EXAMPLES

Preparation of the Isosorbide Bisglycidylether
A vessel was charged with 73.5 g isosorbide and 370 g epichlorohydrin. The solution was heated to 115° C. During a period of 10 h 81 g of a 50% aqueous sodium hydroxide solution were added incrementally to the boiling reaction mixture. During the reaction water and epichlorohydrin were distilled from the reaction mixture. Then the water phase was separated and then distilled to remove unreacted epichlorohydrin at 150° C. under vakuum. To separate the salt from the crude product acetone was added under stirring and the mixture was filtered. After washing a further distillation step took place to remove the acetone. Isosorbide bisglycidyl ether was obtained.

Preparation of Isosorbide Diglyceride

A solution of 83 mmol isosorbide bisglycidyl ether (26.9 g) in 22 ml water is prepared at room temperature (21° C.). 2 ml $H_2SO_4$ (30 wt.-%) is added dropwise. After 1 h, 11 mmol (0.8 g) $Ca(OH)_2$ is added for neutralization. The reaction mixture is then filtered and water is removed under vacuum to yield a light yellow oil (Yield: 20 g)

This polyol can then be esterified according to state of the art methods in order to give the isosorbid glyceryl ether esters.

A second way to obtain the glyceryl derivatives of isosorbide is the opening of the oxirane of the bisglycidyl ether via reaction with a fatty alcohol. For this reason 326 mmol of isosorbide bisglycidyl ether (75 g) is added dropwise to a solution of 1 mol dodecanol (182 g) and as catalyst potassium hydroxide (3.65 g, 65 mmol) at 100° C. Once the reaction is completed, the mixture is filtered, and the non-reacted dodecanol is removed under vacuum to give a yellow paste (Yield: 48 g)

Performance Tests of the Isosorbide Glyceryl Ether Derivatives

A foaming test has been conducted, using a laurylglyceryl ether of isosorbide.

Surfactant Mix:

| | | |
|---|---|---|
| SLES | | 9% |
| Betaine | | 3% |
| Glyceryl ether deriv. | | 2% |
| Dest. Water | | 86% |

All the components were mixed together with a mechanical stirrer.

A 2.0 wt % aqueous solution of this surfactant mix was then prepared with hard water. It was then stirred in a beaker for 10 s at 2000 rpm and the foam volume was evaluated. A sample of the foam obtained was then evaluated for quality aspects. The foam quality was determined with 1-2 the foam height was 5.5 cm.

The invention claimed is:

1. An isosorbide glyceryl ether derivative according to general formula (I)

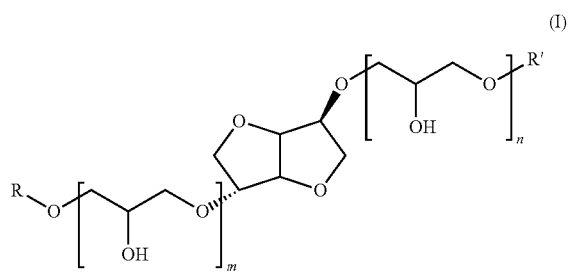

wherein R or R' represent a hydrogen atom, or an alkyl or an acyl group with 6 to 22 C-atoms, and n and m each independently represent zero, or a number from 1 to 4, with the proviso that the sum of n and m is greater than zero.

2. The isosorbide derivative of claim 1, wherein R and/or R' represents a linear, saturated alkyl or an acyl moiety with 10 to 22 C-atoms.

3. A method of preparing a cleanser, detergent or personal care composition, the method comprising adding an isosorbide glyceryl ether derivative according to claim 1 to prepare cleansers, detergents or personal care compositions.

4. The method of claim 3, wherein R and/or R' represents a linear, saturated alkyl moiety with 10 to 22, C-atoms.

5. The method of claim 3, wherein the isosorbide glyceryl derivative is present in amounts from 0.1 to 25 wt %, based on the total weight of the cleanser or detergent.

6. A cleanser, detergent or personal care composition comprising water, a surfactant, and at least 0.1% by weight of at least one isosorbide derivative of claim 1.

7. The isosorbide derivative of claim 1, wherein R and/or R' represents a linear, saturated alkyl or an acyl moiety with 12 to 20 C-atoms.

8. The isosorbide derivative of claim 1, wherein R and/or R' represents a linear, saturated alkyl or an acyl moiety with 14 to 18 C-atoms.

9. The method of claim 3, wherein R and/or R' represents a linear, saturated alkyl moiety with 12 to 20 C-atoms.

10. The method of claim 3, wherein R and/or R' represents a linear, saturated alkyl moiety with 14 to 18 C-atoms.

11. The method of claim 3, wherein the isosorbide glyceryl derivative is present in amounts from 1 to 15 wt %, based on the total weight of the cleanser or detergent.

12. The method of claim 3, wherein the isosorbide glyceryl derivative is present in amounts from 5 to 10 wt %, based on the total weight of the cleanser or detergent.

* * * * *